US007234861B2

(12) United States Patent
Nishimura

(10) Patent No.: US 7,234,861 B2
(45) Date of Patent: Jun. 26, 2007

(54) COOLING MECHANISM, COOLING APPARATUS HAVING COOLING MECHANISM, AND THERMAL ANALYZER EQUIPPED WITH COOLING APPARATUS

(75) Inventor: Shinya Nishimura, Chiba (JP)

(73) Assignee: SII NanoTechnology Inc. (JP)

( * ) Notice: Subject to any disclaimer, the term of this patent is extended or adjusted under 35 U.S.C. 154(b) by 0 days.

(21) Appl. No.: 10/929,859

(22) Filed: Aug. 30, 2004

(65) Prior Publication Data
US 2005/0053115 A1     Mar. 10, 2005

(30) Foreign Application Priority Data
Sep. 4, 2003     (JP)     ............... 2003-313086

(51) Int. Cl.
G01K 17/00     (2006.01)
G01N 25/00     (2006.01)

(52) U.S. Cl. .......................................... 374/33; 374/12

(58) Field of Classification Search ............. 374/10–12
See application file for complete search history.

(56) References Cited

U.S. PATENT DOCUMENTS 4,031,740 A * 6/1977 Achermann .................. 374/31
4,456,389 A * 6/1984 Regenass et al. ............. 374/31
4,892,707 A * 1/1990 Stockton et al. .............. 422/51
5,193,910 A * 3/1993 Kinoshita ..................... 374/45
5,198,752 A * 3/1993 Miyata et al. ............... 324/760
5,484,204 A * 1/1996 Damley ........................ 374/10
5,671,603 A * 9/1997 McCorkle et al. ........... 62/49.2
5,876,118 A * 3/1999 Vogel ........................... 374/11
6,487,866 B1* 12/2002 Fesmire et al. .............. 62/51.1
6,578,367 B1* 6/2003 Schaefer et al. ............. 62/51.1
2002/0018509 A1* 2/2002 Boiarksi ....................... 374/11
2002/0172629 A1* 11/2002 Jahn et al. ................... 422/187

* cited by examiner

Primary Examiner—Diego Gutierrez
Assistant Examiner—Mirellys Jagan
(74) Attorney, Agent, or Firm—Adams & Wilks

(57) ABSTRACT

A thermal analyzer has a heat sink for storing therein a specimen, a heater for heating the heat sink and the specimen, at superheating temperatures, and a cooling mechanism thermally connected to the heat sink for cooling the heat sink and the specimen. The cooling mechanism is comprised of a tubular member having an inlet port for introducing a cooling gas into the tubular member and an outlet port for discharging the cooling gas from the tubular member. A tubular extension is thermaly connected to and extends from the tubular member. An electric cooling device has a cooling head connected to the tubular extension for cooling the cooling mechanism.

6 Claims, 2 Drawing Sheets

COOLING MECHANISM, COOLING APPARATUS HAVING COOLING MECHANISM, AND THERMAL ANALYZER EQUIPPED WITH COOLING APPARATUS

BACKGROUND OF THE INVENTION

1. Field of the Invention

The present invention relates to a cooling apparatus having a cooling mechanism for cooling a heat sink in a thermal analyzer or the like, and to a thermal analyzer, such as a differential scanning calorimeter, equipped with the cooling apparatus.

2. Description of the Related Art

A thermal analyzer such as differential scanning calorimeter includes a heat sink which is under a temperature control, a specimen disposed in the inside of the heat sink, a reference material holder, a heater which heats the heat sink, and a cooling device which cools the heat sink. As such a cooling device, conventionally, there have been known a gas cooling device which performs cooling using a low-temperature gas which is obtained by evaporating liquefied nitrogen or the like (see, for example, Japanese Accepted Patent Publication Hei7(1995)-122619(fourth column, FIG. 1), Japanese Accepted Patent Publication Hei7(1995)-65974 (fourth column, FIG. 1)), and an electric cooling device which incorporates a compressor therein and performs cooling by way of a metal-made cooling member which is cooled by a refrigerant cooled by the compressor. Cooling has been conventionally performed by mounting either one of a cooling members of these gas cooling device and the electric cooling device on a furnace of the thermal analyzer in an exchangeable manner depending on the necessity.

In the conventional differential scanning calorimeter, only one type of cooling device can be mounted on the differential scanning calorimeter and, therefore, it is possible to use only one type of cooling method. Accordingly, when the gas cooling device is used, although cooling can be performed up to −150° C., there have been drawbacks in that it is necessary to replenish liquefied nitrogen which is a refrigerant and, at the same time, when the heat sink is cooled rapidly, the amount of gas consumed is increased.

Further, when the electric cooling device is used, since a refrigerant is hermetically sealed, it is unnecessary to replenish the refrigerant. However, with respect to the inexpensive electric cooling device which exhibits the favorable operability, there has been a drawback in that the cooling of −100° C. or below cannot be performed due to a capacity thereof.

Further, it has been considered cumbersome to exchange a cooling head which covers the heat sink between the cooling head for the electric cooling device and the gas cooling device depending on the use thereof.

SUMMARY OF THE INVENTION

Accordingly, it is an object of the present invention to provide a thermal analyzer provided with a cooling apparatus which can overcome the above-mentioned drawbacks and can perform cooling by suppressing a consumption amount of gas even when the rapid cooling is performed or even when the cooling to a temperature equal to or below −100° C. is performed. In addition, it is an object of the present invention to remove the burden of exchanging the cooling heads depending on the use.

To achieve the above mentioned object, the present invention is directed to a thermal analyzer which measures a change generated in a specimen when the specimen is heated and cooled, the thermal analyzer including a heat sink which stores the specimen therein, a heater which superheats the heat sink, and a cooling mechanism which is brought into thermal contact with the heat sink. The cooling mechanism includes an annular hollow pipe, a pipe which introduces a cooling gas and a pipe which discharges the cooling gas formed in the annular hollow pipe, and a cooling head fixing portion which fixes a cooling head of an electric cooling device. On an inner wall of the annular hollow pipe, fins for enhancing the cooling efficiency are formed. The cooling head fixing portion is brought into thermal contact with an inner wall of a cooling chamber. The annular hollow pipe is fixed to the heat sink by blazing or using bolts such that an end surface of the annular hollow pipe is brought into thermal contact with an upper portion or a lower portion of the heat sink.

Here, the thermal contact implies a contact which forms a thermal flow passage when parts are brought into contact with each other.

As described above, in the cooling device of the present invention, since the cooling mechanism can be used in common by the gas cooling device and the electric cooling device, usually, it is possible to use the electric cooling device at a temperature equal to −10020 C. or above and to use the gas cooling device at a temperature below −100° C. That is, it is unnecessary for a measurer to exchange the cooling members which are connected to respective cooling devices in accordance with the use temperature before measurement.

Further, due to the use of the electric cooling device and the gas cooling device in combination, a load of the gas cooling device can be reduced and, therefore, a consumption amount of gas can be suppressed whereby a load attributed to the replenishment of liquefied nitrogen can be reduced.

Further, due to the use of the electric cooling device and the gas cooling device in combination, the heat sink can be rapidly cooled whereby the cooling time can be shortened, thus realizing the enhancement of the efficiency of the measurement.

DESCRIPTION OF THE PREFERRED EMBODIMENTS

Figure 1:
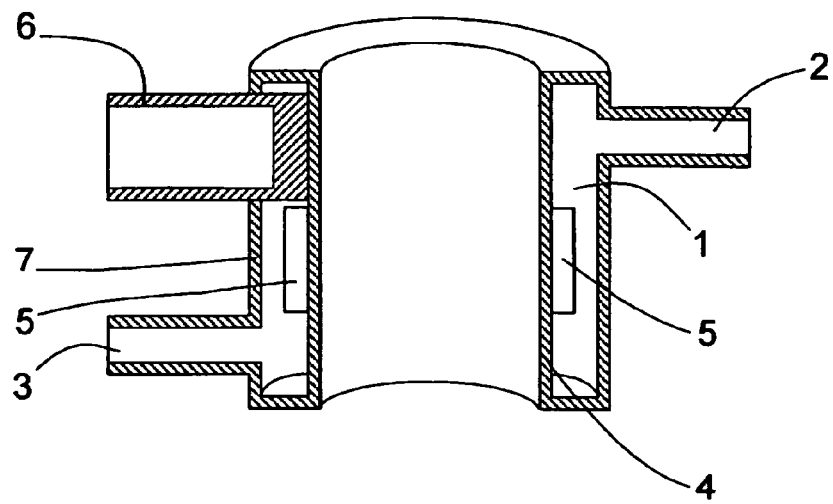
FIG. 1 is a cross-sectional view of a cooling mechanism of the present invention.

FIG. 1 shows a cooling mechanism used in a cooling device which can use a plurality of cooling means in combination.

As shown FIG. 1, the cooling mechanism is constituted of an annular hollow pipe and forms a cavity 1 therein. The cavity 1 is provided with a cooling gas inlet port 2 which allows the introduction of a cooling gas from a gas cooling device and a cooling gas discharge port 3 which allows the discharge of the cooling gas toward the outside. On an inner side of an inner wall 4 of the cooling device, a plurality of plate-like fins 5 is formed for enhancing the cooling efficiency.

An inner surface of the inner wall 4 of the cooling device has the structure in which a bottom surface of a cylindrical cooling head fixing member 6 of the electric cooling device is brought into contact with the inner surface of the inner wall 4 or the cooling head fixing member 6 is integrally formed with the inner wall 4 and hence, the head fixing member 6 is thermally connected with the inner wall of the cooling device. The electric-cooling-device fixing member 6 enables the cooling of the inner wall 4 and an outer wall 7 of the annular hollow pipe through the fixing member 6 by inserting the cylindrical cooling head 11 of the electric cooling device into a recessed portion of the cylindrical fixing member 6.

The electric cooling device is a cooling device which adopts a compressor-type refrigerant circulation. That is, the electric cooling device obtains cooling ability by performing the compression and the adiabatic expansion of the refrigerant using the compressor.

With respect to the manner of using the gas cooling device, the liquefied nitrogen is superheated by the heater. The evaporated gas is introduced into the gas cooling device from the cooling gas inlet port 2 so as to cool the fins 5, the inner wall 4 and the outer wall 7. The gas which is warmed after being used for cooling is discharged from the gas discharge port 3.

Figure 2:
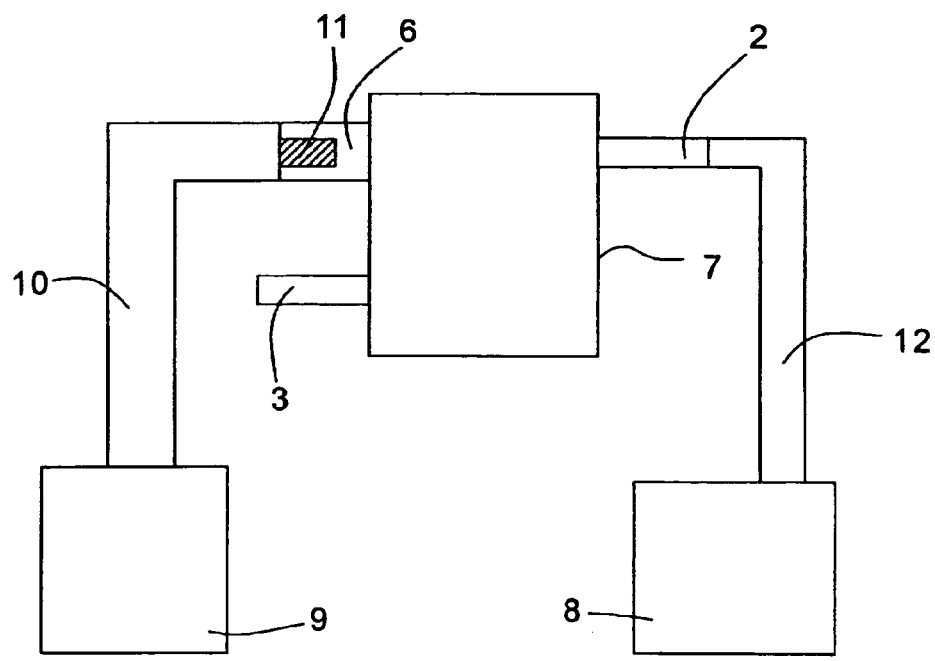
FIG. 2 is a schematic view showing a state in which a cooling device is connected to a cooling mechanism of the present invention.

Next, the connection method of the cooling device is explained in conjunction with FIG. 2. The cooling device of the present invention is characterized in that the electric cooling device 9 and the gas cooling device 8 are used in combination. Since connecting portions of the gas cooling device and the electric cooling device are formed independently whereby it is possible to connect a plurality of cooling devices simultaneously.

In the electric cooling device 9, the refrigerant is circulated in a metal-made pipe 10 so as to cool the cooling head 11 formed on a distal end of the pipe. The cooling head 11 is brought into contact with and is fixed to the electric cooling fixing member 6 so as to cool the whole cooling mechanism.

In the gas cooling device, the cooling gas evaporated in the inside of the gas cooling device is injected into the gas inlet port 2 through a metal pipe 12. The gas which is used for cooling in the inside of the cooling mechanism and is warmed is discharged from the gas discharge port 3.

To perform the rapid cooling during the measurement or during a period from the measurement to the next measurement, it is possible to simultaneously operate the gas cooling device 8 and the electric cooling device 9.

Figure 3:
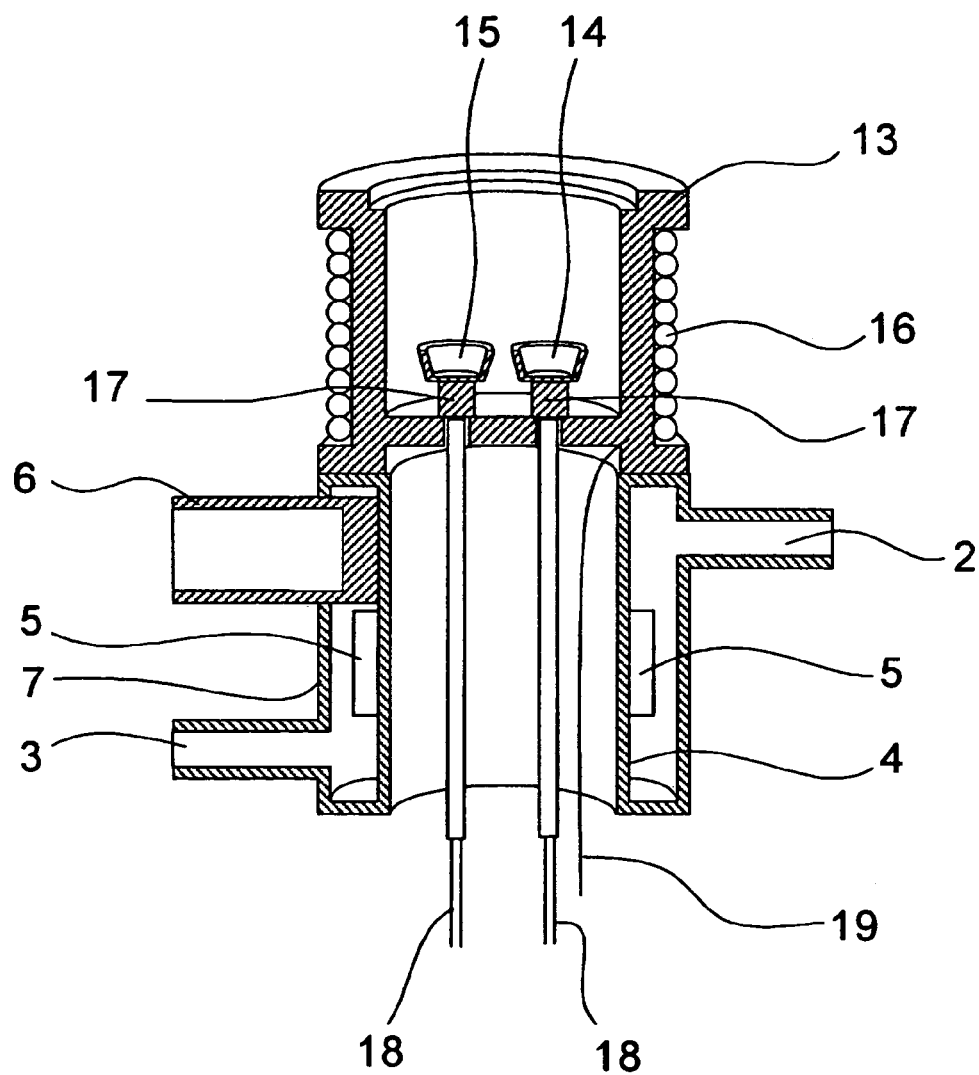
FIG. 3 is a schematic view showing a state in which a differential scanning calorimeter is connected to a cooling machanism of the present invention.

Next, a differential scanning calorimeter which is connected to the cooling device of the present invention is explained in conjunction with FIG. 3.

A specimen holder 14 and a reference material holder 15 are provided in the inside of a heat sink 13. On a side surface of the heat sink 13, a heater 16 which is used for heating and is covered with an insulation coating is wound. Below the specimen holder 14 and the reference material holder 15, differential scanning calorimeters 17 are respectively arranged and the temperature difference is detected by the above-mentioned detector.

To respective differential scanning calorimeters 17 disposed below the specimen and the reference material holder 18, thermocouple fine lines 18 are welded so as to detect the specimen temperature and the temperature difference between the specimen and the reference material and the specimen temperature and the temperature difference are outputted as a heat current.

In the temperature control of the heat sink 13, the temperature of the heat sink 13 is detected using a control thermocouple 19 and a PID control is performed using the heater 16 and the cooling device. Due to such a PID control, electricity is supplied to the heater 16 in accordance with a temperature program set by a measurer and hence, it is possible to accurately control the temperature of the heat sink 13.

In this embodiment, although the cooling device is arranged on a lower surface of the heat sink, it is possible to attain the similar advantageous effects by arranging the cooling device on an upper surface or on a side surface of the heat sink. When the cooling device is arranged on the upper surface of the heat sink, the cooling device is fixed such that a lower portion of the annular hollow pipe is brought into thermal contact with an upper surface of the cylindrical heat sink. Further, when the annular hollow pipe is arranged on the side surface of the heat sink such that the annular hollow pipe covers an outer periphery of the heat sink, a flange portion is formed on an upper end portion of the annular hollow pipe and the flange portion is fixed to the upper surface of the heat sink by bringing them into thermal contact. Accordingly, it is possible to efficiently cool the heat sink.

The cooling device of the present invention can be connected to differential scanning calorimeters and other thermal analyzer.

What is claimed is:

1. A cooling mechanism for cooling a sample stored in a heat sink of a thermal analyzer, the cooling mechanism comprising:

a tubular member having an inner wall and an outer wall for thermal connection to the heat sink of the thermal analyzer and defining a cavity therebetween, an inlet port for connection to a first cooling device to introduce a cooling gas supplied by the first cooling device into the cavity to cool the inner and outer walls, and an outlet port for discharging the cooling gas from the cavity; and a connecting member having a first end extending into the cavity and connected to the inner wall of the tubular member and a second end for removable connection to a second cooling device for cooling the inner and outer walls of the tubular member.

2. A cooling mechanism according to claim 1; wherein the connecting member comprises a tubular portion of the tubular member formed in one piece with the inner wall.

3. A cooling mechanism according to claim 1; wherein the connecting member comprises a tubular extension extending from and removably and thermally connected to the inner wall of the tubular member.

4. A cooling mechanism according to claim 1; wherein the tubular member is generally cylindrical-shaped.

5. A cooling mechanism according to claim 1; wherein each of the inlet port and the outlet port comprises a tubular portion extending from the outer wall of the tubular member and disposed in fluid communication with the cavity.

6. A cooling mechanism according to claim 1; further comprising a plurality of fins mounted on the inner wall of the tubular member for enhancing the cooling efficiency of the inner wall.

* * * * *